United States Patent
Georgeson et al.

(10) Patent No.: US 9,404,898 B1
(45) Date of Patent: Aug. 2, 2016

(54) LASER ULTRASOUND TESTING IN LIMITED-ACCESS AREAS

(71) Applicant: The Boeing Company, Chicago, IL (US)

(72) Inventors: Gary Ernest Georgeson, Tacoma, WA (US); Alan Frank Stewart, Renton, WA (US); William P. Motzer, Seattle, WA (US); Steven Kenneth Brady, Renton, WA (US); Richard H. Bossi, Renton, WA (US); Clarence Lavere Gordon, III, Renton, WA (US)

(73) Assignee: THE BOEING COMPANY, Chicago, IL (US)

( * ) Notice: Subject to any disclaimer, the term of this patent is extended or adjusted under 35 U.S.C. 154(b) by 337 days.

(21) Appl. No.: 13/834,552

(22) Filed: Mar. 15, 2013

(51) Int. Cl.
| G01N 29/34 | (2006.01) |
| G01N 29/26 | (2006.01) |
| G01N 29/24 | (2006.01) |
| G01N 29/22 | (2006.01) |
| G01N 29/265 | (2006.01) |

(52) U.S. Cl.
CPC .............. *G01N 29/34* (2013.01); *G01N 29/225* (2013.01); *G01N 29/2418* (2013.01); *G01N 29/265* (2013.01)

(58) Field of Classification Search
CPC .............. G01N 29/225; G01N 29/343; G01N 29/2418; G01N 29/043; G01N 29/11; G01N 29/4472; G01N 29/265; G01N 29/46
USPC ........... 73/583–584, 618–621, 634, 655–656, 73/643
See application file for complete search history.

(56) References Cited

U.S. PATENT DOCUMENTS

| 5,679,899 | A  | * | 10/1997 | Webster et al. ................ 73/656 |
| 6,078,397 | A  |   | 6/2000  | Monchalin et al. |
| 6,144,685 | A  | * | 11/2000 | Iwasa et al. ................ 372/50.12 |
| 6,637,266 | B1 | * | 10/2003 | Froom ............................ 73/583 |
| 6,901,157 | B2 | * | 5/2005  | Ogawa .......................... 382/128 |
| 7,467,560 | B2 | * | 12/2008 | Silverman et al. ............ 73/865.8 |
| 7,784,348 | B2 | * | 8/2010  | Dubois et al. ................... 73/621 |
| 7,859,655 | B2 | * | 12/2010 | Troy ........................ G01C 1/04 348/169 |
| 8,243,280 | B2 |   | 8/2012  | Dubois et al. |
| 8,332,165 | B1 | * | 12/2012 | Tat et al. ........................ 702/39 |
| 8,713,998 | B2 | * | 5/2014  | Troy et al. ...................... 73/104 |
| 8,930,042 | B2 | * | 1/2015  | Jang et al. ........................ 701/2 |
| 9,043,146 | B2 | * | 5/2015  | Troy ........................ G01S 17/46 382/103 |
| 9,188,566 | B2 | * | 11/2015 | Georgeson ......... G01N 29/2418 |
| 2003/0228916 | A1 | * | 12/2003 | Simeray .......................... 463/62 |

(Continued)

OTHER PUBLICATIONS

Backes et al., "The Multifunction automated Crawling System (MACS)", Proceeding of the 1997 IEEE International Conference on Robotics and Automation, Albuquerque, New Mexico, Apr. 1997.*

(Continued)

*Primary Examiner* — Helen Kwok
(74) *Attorney, Agent, or Firm* — Yee & Associates, P.C.

(57) ABSTRACT

A method and apparatus for inspecting a structure. In one illustrative embodiment, an apparatus comprises a laser system located outside of an area that includes a region of a structure to be inspected, a mobile platform located within the area to be inspected, and a projection system associated with the mobile platform. The laser system is configured to generate a laser beam. The projection system receives the laser beam and projects the laser beam onto a surface of the region of the structure. The laser beam causes a number of ultrasonic waves to form within the structure.

19 Claims, 10 Drawing Sheets

(56) References Cited

U.S. PATENT DOCUMENTS

| | | | |
|---|---|---|---|
| 2004/0154402 A1* | 8/2004 | Drake, Jr. | G01B 11/161 73/621 |
| 2009/0081923 A1* | 3/2009 | Dooley | A63F 9/143 446/456 |
| 2010/0085437 A1* | 4/2010 | Troy | G01S 5/163 348/211.7 |
| 2010/0097183 A1* | 4/2010 | Pollema | G05D 3/12 340/10.1 |
| 2010/0250189 A1* | 9/2010 | Brown | F41G 3/06 702/181 |
| 2011/0054694 A1* | 3/2011 | Munk | B25B 11/02 700/275 |
| 2011/0282483 A1* | 11/2011 | Simonetti | G05B 19/402 700/114 |
| 2012/0320372 A1* | 12/2012 | Troy | B64F 5/0045 356/237.2 |
| 2013/0041544 A1* | 2/2013 | Troy | G05D 1/0246 701/23 |
| 2013/0333472 A1* | 12/2013 | Georgeson et al. | 73/584 |
| 2014/0116146 A1* | 5/2014 | Bossi et al. | 73/643 |

OTHER PUBLICATIONS

Georgeson et al., "Ultrasound Inspection System of Limited Access Composite Structures," U.S. Appl. No. 13/526,698, filed Jun. 19, 2012, 56 pages.

Bossi et al., "Ultrasound Inspection System for Inspecting a Test Object with Non-Planar Features," U.S. Appl. No. 13/596,977, filed Aug. 28, 2012, 80 pages.

Troy et al., "Autonomous Non-Destructive Evaluation System for Aircraft Structures," U.S. Appl. No. 13/160,238, filed Jun. 14, 2011, 57 pages.

Addison, Jr. et al., "Laser-Based Ultrasound for Remote and Limited-Access Inspection Applications," AFRL-ML-WP-TR-2001-4061, Rockwell Science Center, LLC, Air Force Research Laboratory, Dec. 2000, 112 pages.

Nelson et al., "Enhanced Laser Generated Ultrasound," AFRL-ML-WP-TR-1998-4127, Boeing Information, Space & Defense Systems, Air Force Research Laboratory, Jul. 1998, 326 pages.

* cited by examiner

LASER ULTRASOUND TESTING IN LIMITED-ACCESS AREAS

BACKGROUND INFORMATION

1. Field

The present disclosure relates generally to laser ultrasound testing and, in particular, to the laser ultrasound testing of composite structures. Still more particularly, the present disclosure relates to an apparatus, system, and method for using laser ultrasound testing to inspect regions of interest in areas to which access is limited.

2. Background

A laser ultrasound testing (UT) system is a nondestructive testing (NDT) system that may be used to test structures, such as composite structures, for undesired inconsistencies. A nondestructive testing system may also be referred to as a nondestructive inspection (NDI) system or a nondestructive evaluation (NDE) system.

Typically, a laser ultrasound testing system uses a laser beam to induce ultrasound within a composite structure. The laser beam may be a pulsed laser beam. The laser beam may be directed towards a location on a surface of a composite structure. When the laser beam encounters the surface of the composite structure, ultrasonic waves are formed in the composite structure.

The laser ultrasound testing system is capable of detecting these ultrasonic waves and using the detected ultrasonic waves to generate data about the composite structure. This data may then be used to identify information about the composite structure such as, for example, without limitation, a thickness of the composite structure, a material composition of the composite structure, an indication of whether any undesired inconsistencies are present on and/or in the composite structure, and/or other types of information.

In certain situations, a region of interest in a composite structure that is located in an area to which access is limited may need to be inspected. As one illustrative example, the bays formed by the spars of a horizontal stabilizer may be difficult to inspect. Some currently available traditional ultrasound systems may use ultrasonic arrays mounted to robotic arms or robotic crawlers that can be moved within the bays. However, these traditional ultrasound systems may be unable to handle variations in the shapes of the surfaces of these bays as well as desired. For example, these traditional ultrasound systems may be unable to handle the non-precise radii of curvature as well as desired.

Laser ultrasound testing systems may be able to handle variations in the shapes of surfaces. However, the size and/or weight of some currently available laser ultrasound testing systems may prevent these testing systems from being used in confined areas and/or other types of limited-access areas. For example, the types of laser ultrasound testing systems that may be needed to inspect a certain composite structure at the production level may require a large robotic cell. A robotic cell includes a robot, a controller, and/or other peripheral equipment. In some cases, the large robotic cell may be unable to move into and/or fit within certain areas.

Additionally, in some cases, higher power laser ultrasound testing systems require that testing be performed in areas or rooms that have shielding or some other type of protection for the eyes. Ensuring this type of protection may increase the expense of testing more than desired. The increased expense may reduce the feasibility of using these types of testing systems at the production level, or manufacturing level, of a composite structure.

Some lower power laser ultrasound testing systems may be used without requiring shielding. However, these types of testing systems may have a lower signal-to-noise ratio than desired. Consequently, the data generated using these types of testing systems may be less accurate and/or reliable than desired. Therefore, it would be desirable to have a method and apparatus that takes into account at least some of the issues discussed above, as well as other possible issues.

SUMMARY

In one illustrative embodiment, an apparatus comprises a laser system located outside of an area that includes a region of a structure to be inspected, a mobile platform located within the area, and a projection system associated with the mobile platform. The laser system is configured to generate a laser beam. The projection system receives the laser beam and projects the laser beam onto a surface of the region of the structure. The laser beam causes a number of ultrasonic waves to form within the structure.

In another illustrative embodiment, a laser ultrasound testing system comprises a laser system located outside of an area, a mobile platform located within the area, a projection system associated with the mobile platform, and an alignment system. The area includes a region of a structure to be inspected. The laser system is configured to emit a laser beam and a detection laser beam through an output of the laser system. The projection system receives the laser beam and the detection laser beam and projects the laser beam and the detection laser beam onto a surface of the region of the structure. The laser beam causes a number of ultrasonic waves to form within the structure. The alignment system is configured to direct the laser beam and the detection laser beam from an output of the laser system towards the projection system.

In yet another illustrative embodiment, a method is provided for inspecting a structure. A mobile platform is positioned within an area that includes a region of the structure to be inspected. A laser beam is emitted from a laser system located outside of the area towards a projection system associated with the mobile platform. The laser beam is projected onto a surface of the region of the structure at a location selected for inspection using the projection system. A number of ultrasonic waves are formed in the structure in response to the laser beam impacting the surface.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account different considerations. For example, the illustrative embodiments recognize and take into account that an articulated tube may be used to guide a laser beam generated by a laser ultrasound testing system to a location remote to the laser ultrasound testing system. The articulated tube may allow the laser beam to be emitted within otherwise hard to reach locations. In other words, the articulated tube may extend the reach of the laser ultrasound testing system.

However, the illustrative embodiments recognize and take into account that the length of the articulated tube and the joints of the tube may limit the areas into which the articulated tube may enter. Consequently, the illustrative embodiments recognize that it may be desirable to have a laser ultrasound testing system capable of inspecting regions of interest that are located in areas limited-access areas.

Figure 1:
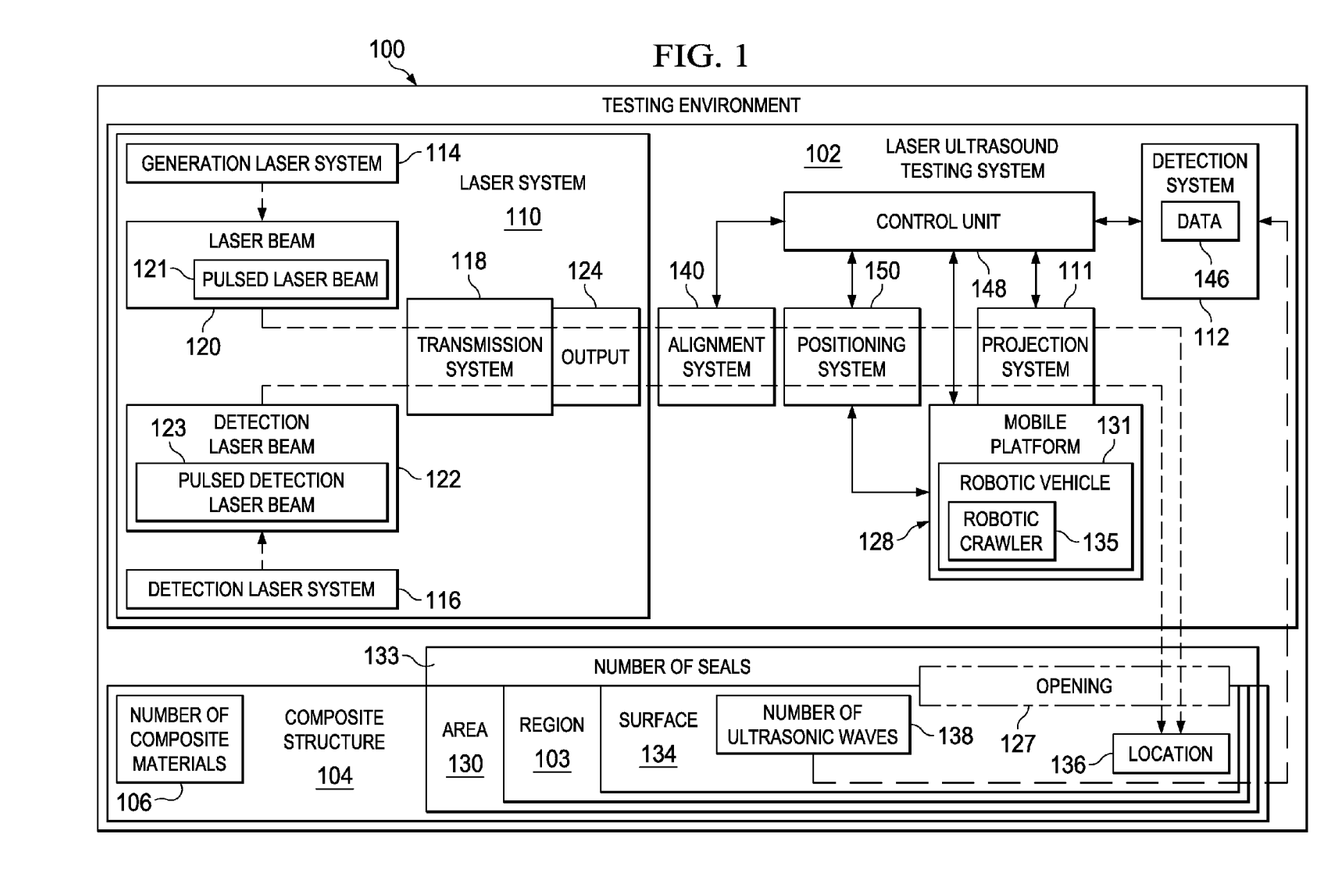
FIG. 1 is an illustration of a testing environment in the form of a block diagram in accordance with an illustrative embodiment.

With reference now to FIG. 1, an illustration of a testing environment in the form of a block diagram is depicted in accordance with an illustrative embodiment. In FIG. 1, testing environment 100 is an example of an environment in which laser ultrasound testing system 102 may be used to inspect a region of interest on or within a structure.

For example, laser ultrasound testing system 102 may be used to inspect region 103 of composite structure 104. Composite structure 104 may be comprised of number of composite materials 106. As used herein, a "number of" items means one or more materials. In this manner, number of composite materials 106 may include one or more composite materials. Each of these composite materials may be comprised of a matrix material and a reinforcement material. In some cases, composite structure 104 may include one or more materials in addition to number of composite materials 106.

Laser ultrasound testing system 102 is a nondestructive testing (NDT) system in this illustrative example. As depicted, laser ultrasound testing system 102 includes laser system 110, projection system 111, and detection system 112. Laser system 110 may include generation laser system 114, detection laser system 116, and, in some cases, transmission system 118.

Generation laser system 114 generates laser beam 120. Laser beam 120 may take the form of, for example, pulsed laser beam 121. Pulsed laser beam 121 is formed by pulses of laser energy. In other words, pulsed laser beam 121 is formed by pulses of light that are emitted in the form of a beam. Similarly, detection laser system 116 generates detection laser beam 122. Detection laser beam 122 may take the form of, for example, pulsed detection laser beam 123.

In one illustrative example, generation laser system 114 and detection laser system 116 may be implemented using a carbon dioxide ($CO_2$) laser system. In another illustrative example, generation laser system 114 and detection laser system 116 may be implemented using an Ytterbium-doped fiber laser system or some other type of laser system. Of course, in other illustrative examples, generation laser system 114 and detection laser system 116 may be implemented using some other type of laser system.

Laser beam 120 and detection laser beam 122 may be emitted from laser system 110 at output 124. Output 124 may be the point at which laser beam 120 and detection laser beam 122 enter free space, or air. In some illustrative examples, laser beam 120 and detection laser beam 122 may be emitted through output 124 using transmission system 118. Transmission system 118 may be configured to guide laser beam 120 and detection laser beam 122 from generation laser system 114 and detection laser system 116, respectively, to output 124.

Transmission system 118 may take a number of different forms. In one illustrative example, transmission system 118 takes the form of, for example, without limitation, a waveguide, a series of connected waveguides, a fiberoptic system, or some other type of structure. When transmission system 118 is used, output 124 of laser system 110 may be the output of transmission system 118.

Laser system 110 may be positioned relative to composite structure 104 such that output 124 of laser system 110 is positioned at an access point for area 130. Region 103 of composite structure 104 to be inspected may be located within area 130. Area 130 may be an area to which access is limited. Area 130 may be, for example, without limitation, a bay, a compartment, a hollow portion, a cavity, or some other type of limited-access area.

Laser system 110 may be located outside of area 130. In one illustrative example, area 130 may be an area within a wing box of a wing for an aircraft. Laser system 110 may be unable to enter this bay. Consequently, when inspection of region 103 within area 130 is to be performed, mobile platform 128 may be moved into area 130. In another illustrative example, area 130 may be a portion of the bay within a spar box. Laser system 110 may be positioned within the bay, but outside of area 130. Mobile platform 128 may be positioned within area 130 for inspection. In this manner, area 130 may be any type of area that is inaccessible to laser system 110 or difficult for laser system 110 to reach.

Mobile platform 128 may be any type of platform capable of movement. In one illustrative example, mobile platform 128 may take the form of robotic vehicle 131. Robotic vehicle 131 may be, for example, robotic crawler 135.

Once mobile platform 128 has been moved into area 130, area 130 may be lightproofed. As used herein, area 130 being "lightproofed" means that area 130 may be made impenetrable to light. In other words, light may be prevented from entering area 130 and/or escaping area 130. Area 130 may be lightproofed in a number of different ways. In one illustrative example, number of seals 133 may be used to lightproof area 130. As used herein, a "seal," such as one of number of seals 133, may be a cover, a cap, a foam insert, a rubber insert, or some other type of structural element that can be used to provide a light-tight seal at some portion of area 130.

In this illustrative example, area 130 may be lightproofed such that the only light that may enter and/or escape area 130 may be through opening 127. Opening 127 is an access point through which area 130 may be accessed. Laser system 110 may be positioned such that output 124 of laser system 110 is positioned at opening 127. The only light that may enter area 130 may be laser beam 120 and detection laser beam 122 emitted through output 124 into opening 127. Further, the only light that may escape area 130 may be through opening 127 back through output 124.

Laser beam 120 and detection laser beam 122 enter area 130 through opening 127 and are directed towards projection system 111. Projection system 111 is associated with mobile platform 128 in this illustrative example. When one component is "associated" with another component, the association is a physical association in the depicted examples.

For example, a first component, such as projection system 111, may be considered to be associated with a second component, such as mobile platform 128, by being secured to the second component, bonded to the second component, mounted to the second component, welded to the second component, fastened to the second component, and/or connected to the second component in some other suitable manner. The first component also may be connected to the second component using a third component. In some cases, the first component may be considered to be associated with the second component by being formed as part of and/or as an extension of the second component.

Projection system 111 is configured to receive laser beam 120 and detection laser beam 122. Further, projection system 111 is configured to project laser beam 120 and detection laser beam 122 onto surface 134 of region 103 within area 130. In this illustrative example, projection system 111 projects laser beam 120 and detection laser beam 122 onto a same location 136 on surface 134. However, in other illustrative examples, laser beam 120 and detection laser beam 122 may be projected onto different locations on surface 134.

Projection system 111 may be implemented in a number of different ways. Projection system 111 may be implemented using at least one of a mirror, a prism, a lens, a rotating diffraction grating, a mirror-based gimbal system, a beam-director unit, a galvanometer, a mirror galvanometer, a galvanometer scanner, or some other type of device.

As used herein, the phrase "at least one of," when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required.

For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

In some illustrative examples, laser ultrasound testing system 102 may also include alignment system 140. Alignment system 140 may be used to ensure that laser beam 120 and detection laser beam 122 emitted through output 124 at opening 127 are received by projection system 111. In other words, alignment system 140 may be configured to align laser beam 120 and detection laser beam 122 with projection system 111. This type of alignment may require one or more changes in the direction of the path for laser beam 120 and/or detection laser beam 122.

Alignment system 140 may be implemented in a number of different ways. Alignment system 140 may include, for example, without limitation, at least one of a mirror, a prism, a lens, a rotating diffraction grating, a mirror-based gimbal system, a beam-director unit, a galvanometer, a mirror galvanometer, a galvanometer scanner, a detector, a quadrant cell detector, or some other type of device.

Depending on the implementation, a portion of alignment system 140 may be associated with output 124 of laser system 110 and/or with number of seals 133 around or within opening 127. A "portion" of alignment system 140 may be some or all of alignment system 140.

In some cases, a portion of alignment system 140 may be associated with mobile platform 128. In other illustrative examples, a portion of alignment system 140 may be associated with another platform located within area 130. This other platform may be configured to remain stationary within area 130 during inspection or may be capable of movement within area 130.

Alignment system 140 ensures that laser beam 120 and detection laser beam 122 are received by projection system 111 such that projection system 111 may project laser beam 120 and detection laser beam 122 onto surface 134. In response to laser beam 120 impacting surface 134, number of ultrasonic waves 138 may be formed within composite structure 104. Number of ultrasonic waves 138 may be detected using detection system 112 and detection laser beam 122.

For example, when detection laser beam 122 encounters at least one ultrasonic wave in number of ultrasonic waves 138, detection laser beam 122 may be altered. The alteration may include a change in at least one of the path, intensity, phase, frequency, or some other feature of detection laser beam 122.

The alteration to detection laser beam 122 is detected using detection system 112. In one illustrative example, detection system 112 takes the form of an interferometry-based detection system. In one illustrative example, laser system 110 and detection system 112 may be associated with a platform located remotely with respect to area 130 in composite structure 104.

Detection system 112 generates data 146 in response to the detection of detection laser beam 122. Data 146 may be used to identify information about composite structure 104. This information may include, for example, without limitation, a thickness of composite structure 104, a material composition of composite structure 104, an indication of whether any undesired inconsistencies are present on and/or in composite structure 104, and/or other types of information.

Laser system 110, projection system 111, detection system 112, and alignment system 140 may be controlled using control unit 148. Control unit 148 may be implemented using hardware, software, or a combination of the two. In one illustrative example, control unit 148 may be implemented within a computer system comprising a number of computers. When more than one computer is present in the computer system, these computers may be in communication with each other.

In another illustrative example, control unit 148 may be implemented using a number of processors, a multi-processor core, and/or some other type of processor, depending on the implementation. In some cases, control unit 148 may be implemented using a circuit system, an application specific integrated circuit (ASIC), a programmable logic device, or some other suitable type of hardware unit.

Depending on the implementation, a portion of control unit 148 may be associated with laser system 110. In some cases, a portion of control unit 148 may be associated with mobile platform 128. For example, a portion of control unit 148 may be integrated in the controller for robotic vehicle 131.

In other cases, at least a portion of control unit 148 may be implemented separately from laser system 110, mobile platform 128, projection system 111, and detection system 112. Laser system 110, mobile platform 128, projection system 111, and detection system 112 may be configured to receive commands from and/or send data to control unit 148 using a number of communications links. These communications links may include, for example, without limitation, a number of wired communications links, a number of wireless communications links, a number of optical communications links, and/or other types of communications links.

Control unit 148 may also be used to control the movement of mobile platform 128 within area 130. Control unit 148 may use, for example, without limitation, an image, a scan, a computer-aided design (CAD) model, and/or other types of data for composite structure 104 to generate commands for guiding mobile platform 128 within area 130. In some cases, control unit 148 may use data received from positioning system 150 to guide mobile platform 128 within area 130.

In one illustrative example, at least a portion of positioning system 150 is associated with mobile platform 128. Positioning system 150 may comprise, for example, without limitation, a laser device, an imaging system, a motion capture system, a laser detection system, and/or other types of systems or devices that may be used to monitor the location of mobile platform 128 within area 130. In this manner, the current location of mobile platform 128 within area 130 at any given point in time may be used to guide mobile platform 128 to a next location within area 130.

The illustration of testing environment 100 in FIG. 1 is not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

For example, in some illustrative examples, transmission system 118 may be optional. In other words, laser system 110 may be configured to emit laser beam 120 and detection laser beam 122 directly into area 130 through opening 127.

In other illustrative examples, laser system 110 may be configured to move outside of composite structure 104 such that the direction in which laser beam 120 and/or detection laser beam 122 enters area 130 may be changed. In some cases, alignment system 140 may be used to change the direction in which laser beam 120 and detection laser beam 122 are steered within area 130.

Figure 2:
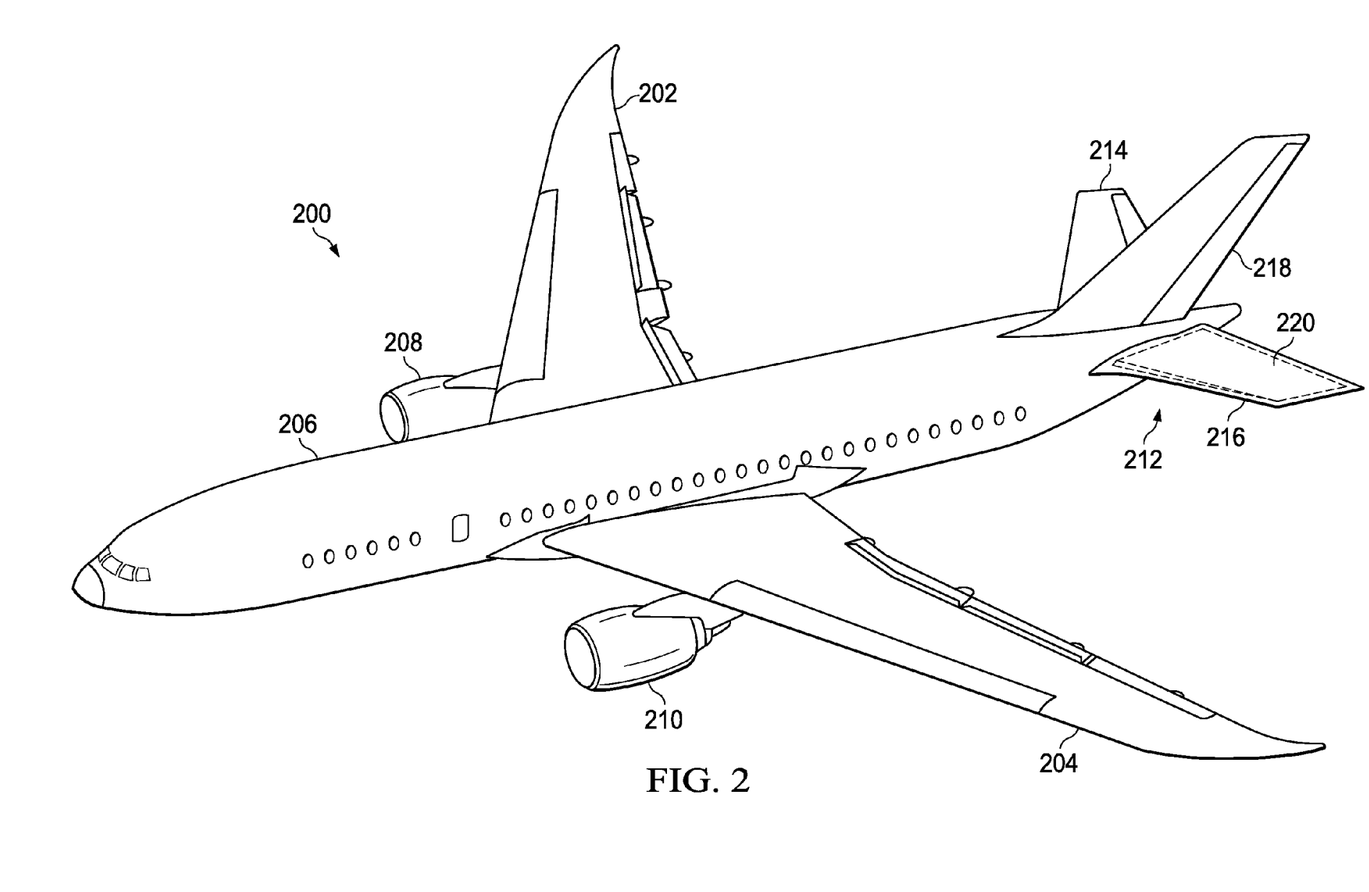
FIG. 2 is an illustration of an aircraft in accordance with an illustrative embodiment.

With reference now to FIG. 2, an illustration of an aircraft is depicted in accordance with an illustrative embodiment. In this illustrative example, aircraft 200 has wing 202 and wing 204 attached to body 206. Aircraft 200 includes engine 208 attached to wing 202 and engine 210 attached to wing 204.

Body 206 has tail section 212. Horizontal stabilizer 214, horizontal stabilizer 216, and vertical stabilizer 218 are attached to tail section 212 of body 206. As depicted, horizontal stabilizer 216 may have composite frame 220 (shown in phantom in this view). Composite frame 220 may be an example of one implementation for composite structure 104 in FIG. 1. Composite frame 220 may be inspected using a laser ultrasound testing system, such as laser ultrasound testing system 102 in FIG. 1.

Figure 3:
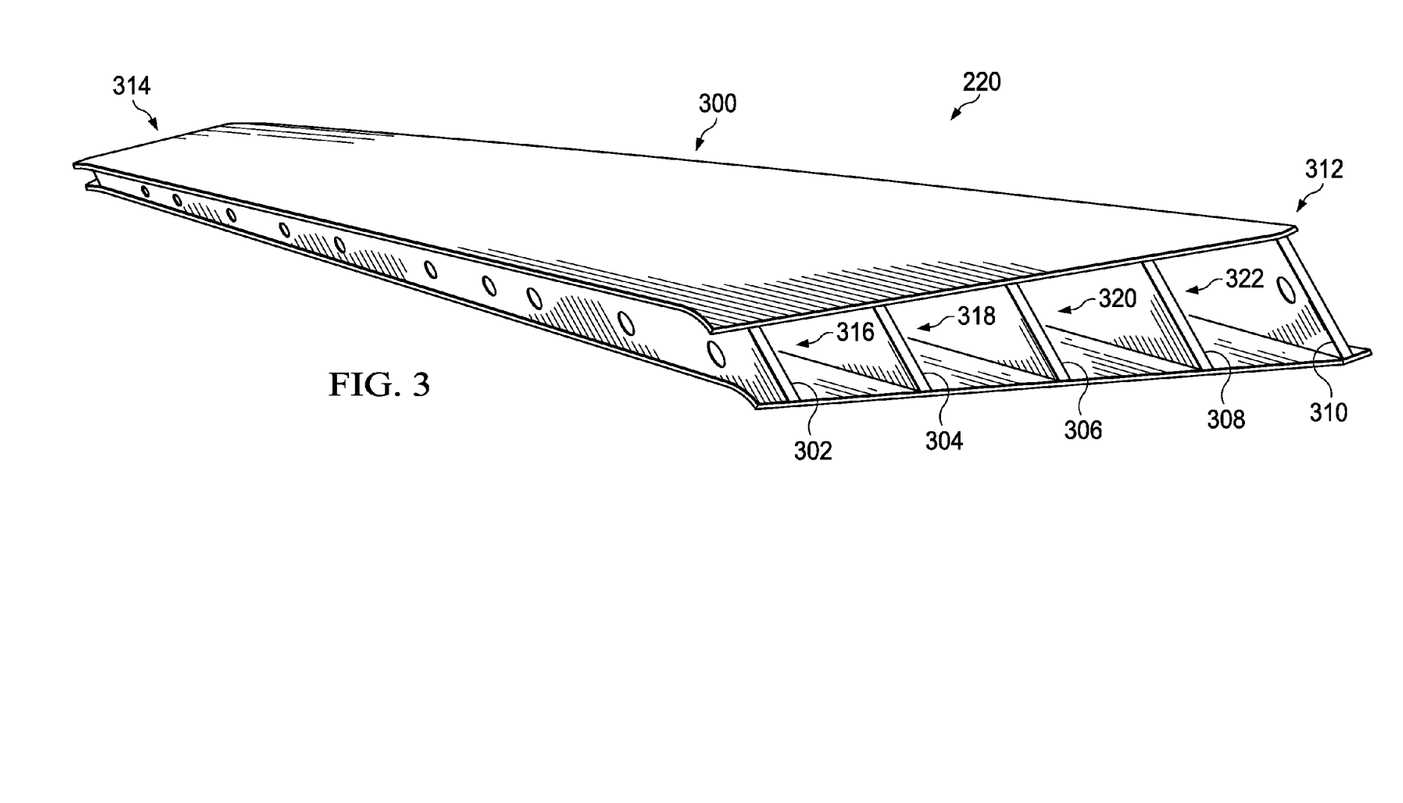
FIG. 3 is an illustration of an enlarged view of a composite frame in accordance with an illustrative embodiment.

With reference now to FIG. 3, an illustration of an enlarged view of composite frame 220 from FIG. 2 is depicted in accordance with an illustrative embodiment. In some illustrative examples, composite frame 220 may be referred to as spar box 300.

As depicted, composite frame 220 includes spars 302, 304, 306, 308, and 310. Spars 302, 304, 306, 308, and 310 extend from end 312 of composite frame 220 to end 314 of composite frame 220 in this example. Spars 302, 304, 306, 308, and 310 define bays 316, 318, 320, and 322. Each of these bays may be an example of an implementation for area 130 in FIG. 1.

In this illustrative example, the width and height of bays 316, 318, 320, and 322 decreases from end 312 to end 314. A mobile platform, such as mobile platform 128 in FIG. 1, may be used to carry a projection system, such as projection system 111 in FIG. 1, into each of these bays. The projection system may be used to scan regions of interest within each of these bays.

Figure 4:
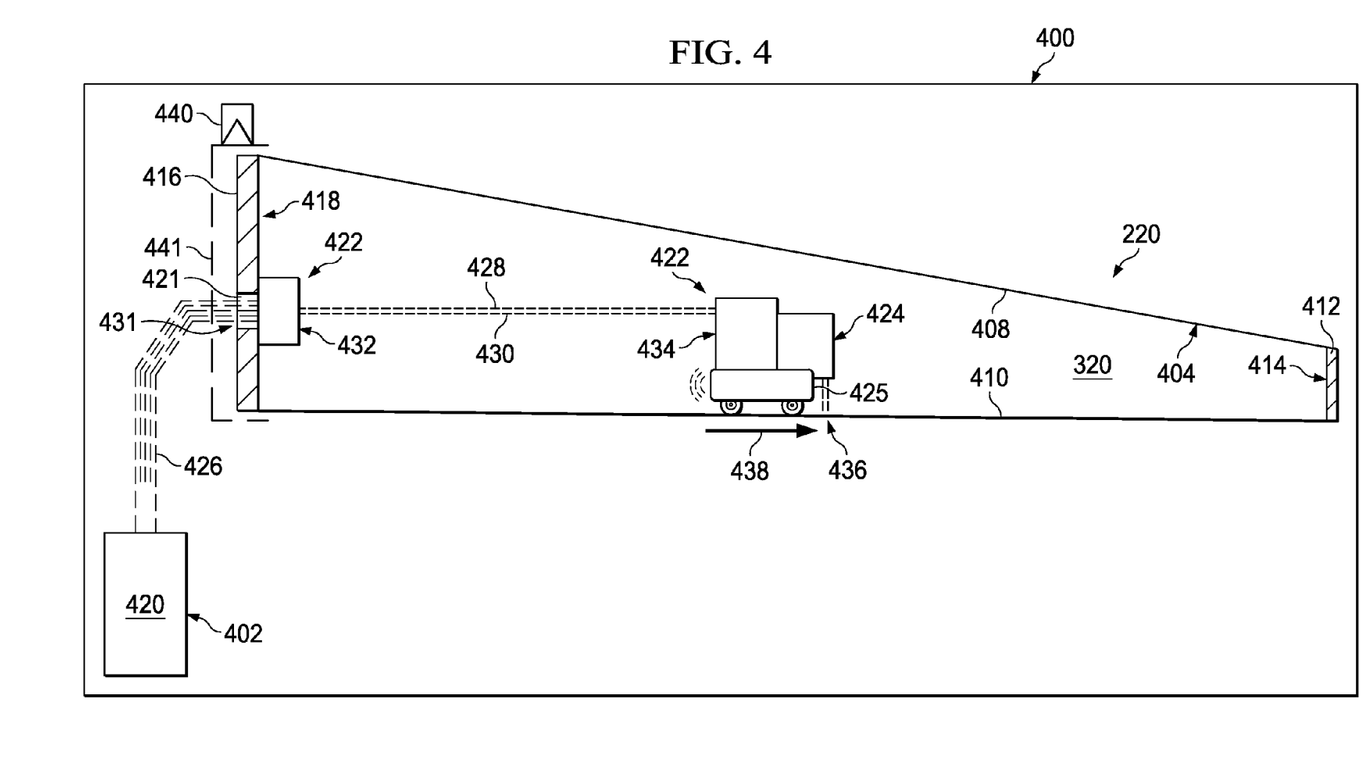
FIG. 4 is an illustration of a testing environment in accordance with an illustrative embodiment.

With reference now to FIG. 4, an illustration of a testing environment is depicted in accordance with an illustrative embodiment. Testing environment 400 is an example of one implementation for testing environment 100 in FIG. 1.

Within testing environment 400, laser ultrasound testing system 402 is used to inspect composite frame 220. In particular, laser ultrasound testing system 402 is used to inspect a region of interest within bay 320 of composite frame 220. Laser ultrasound testing system 402 may be an example of one implementation for laser ultrasound testing system 102 in FIG. 1.

As depicted, interior surface 404 of bay 320 includes first surface 408 and second surface 410, as well as the inner surfaces of spar 306 and spar 308 from FIG. 3 (not shown in this view). Prior to inspection within bay 320, seal 412 is used to lightproof end 414 of bay 320 and seal 416 is used to lightproof end 418 of bay 320. Seal 416 has opening 421, which allows access into bay 320.

In this illustrative example, laser ultrasound testing system 402 includes laser system 420, alignment system 422, projection system 424, and robotic crawler 425. Laser system 420, alignment system 422, projection system 424, and robotic crawler 425 may be examples of implementations for laser system 110, alignment system 140, projection system 111, and robotic crawler 135, respectively, in FIG. 1.

Laser system 420 is configured to generate laser beam 428 and detection laser beam 430. Laser system 420 may include articulated beam transfer assembly 426 in this example. Articulated beam transfer assembly 426 is an example of one implementation for transmission system 118 in FIG. 1. Articulated beam transfer assembly 426 may include any number of optical waveguides that provide collimation, beam combining optical elements, beam tubes, mirrors, and/or other types of optical elements. Articulated beam transfer assembly 426 is used to guide laser beam 428 and detection laser beam 430 generated by laser system 420 to output 431 of articulated beam transfer assembly 426 positioned at opening 421.

As depicted, output 431 of articulated beam transfer assembly 426 is positioned at opening 421 such that laser beam 428 and detection laser beam 430 may enter bay 320 through opening 421. In this illustrative example, alignment system 422 is used to ensure that laser beam 428 and detection laser beam 430 are received at projection system 424.

Alignment system 422 includes first setup 432 and second setup 434. First setup 432 may have a fixed position relative to output 431 of articulated beam transfer assembly 426. As depicted, first setup 432 is associated with seal 416, and second setup 434 is associated with robotic crawler 425 in this illustrative example.

First setup 432 is used to ensure that laser beam 428 and detection laser beam 430, emitted at output 431, are directed, or steered, towards second setup 434. Further, second setup 434 is used to ensure that laser beam 428 and detection laser beam 430 are directed, or steered, towards projection system 424.

As depicted, projection system 424 is associated with robotic crawler 425. In response to receiving laser beam 428 and detection laser beam 430, projection system 424 projects laser beam 428 and detection laser beam 430 onto second surface 410 at location 436. With both laser beam 428 and detection laser beam 430 being pointed at location 436, location 436 may be inspected for the presence of any undesired inconsistencies. Robotic crawler 425 may move in the direction of arrow 438 such that other locations on second surface 410 within bay 320 may be inspected.

In this illustrative example, detector system 440 may be associated with seal 416. Detector system 440 may be implemented using one or more detectors positioned around seal 416. Detector system 440 may be used to determine whether any light from laser beam 428 and/or detection laser beam 430 escapes bay 320 past seal 416. If detector system 440 detects light having intensity beyond some selected threshold, laser system 420 may halt operation until bay 320 has been properly sealed and lightproofed.

In one illustrative example, detector system 440 may be implemented using at least two detectors positioned between seal 416 and secondary seal 441. Secondary seal 441 may be used to ensure that detector system 440 has a dynamic range sufficient to maintain a signal to noise ratio within a desired range in testing environment 400. Secondary seal 441 may take the form of, for example, without limitation, a shroud.

In this illustrative example, laser beam 428 and detection laser beam 430 are depicted as being propagated towards robotic crawler 425 in free-space. However, in other illustrative examples, laser beam 428 and detection laser beam 430 may be propagated from output 431 of articulated beam transfer assembly 426 to robotic crawler 425 though one or more physical waveguides. As one illustrative example, an articulated waveguide may be used. In another example, a series of connected waveguides may be used.

Figure 5:
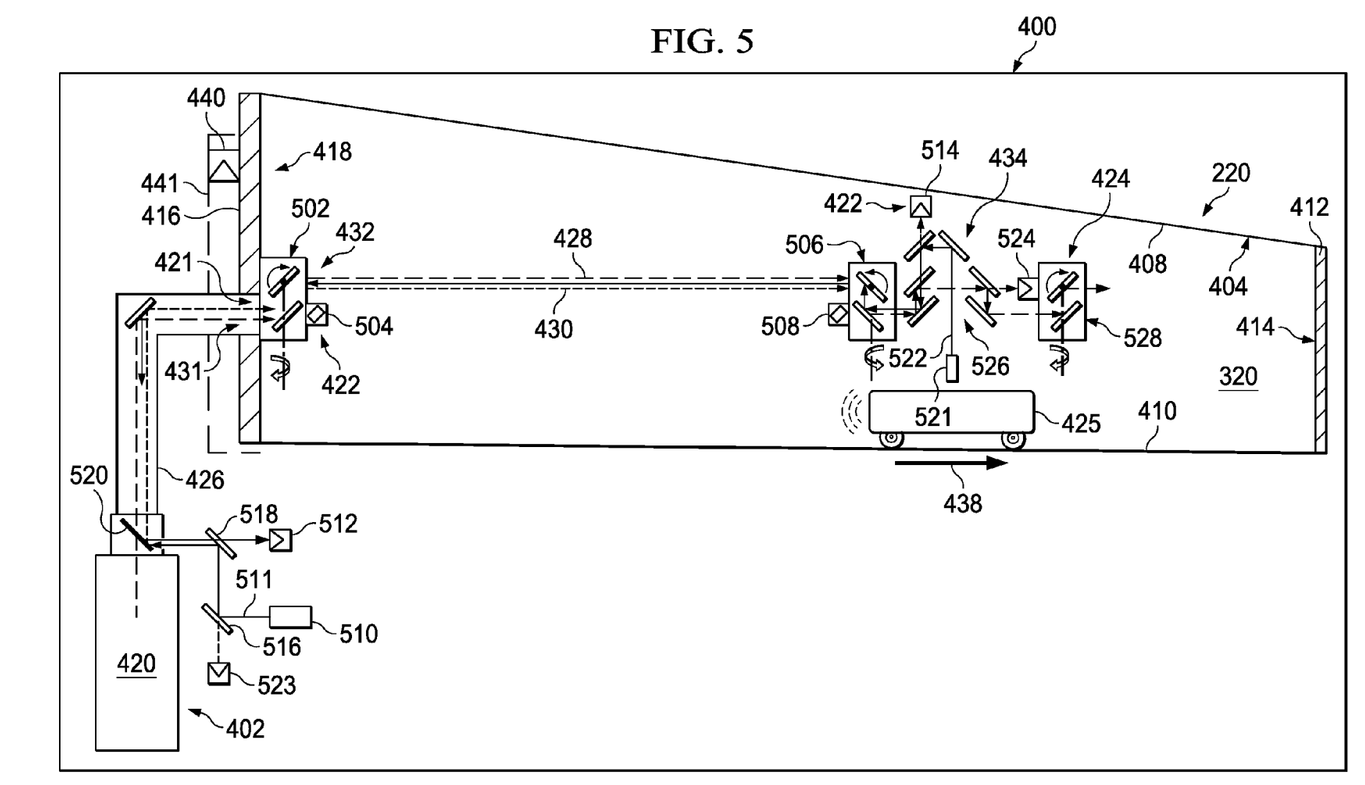
FIG. 5 is an illustration of one configuration for a laser ultrasound testing system in accordance with an illustrative embodiment.

With reference now to FIG. 5, an illustration of one configuration for laser ultrasound testing system 402 is depicted in accordance with an illustrative embodiment. As depicted in FIG. 5, first setup 432 of alignment system 422 includes projection head 502 and corner cube 504. Second setup 434 of alignment system 422 includes receiver head 506 and corner cube 508. Additionally, alignment system 422 may also include first laser device 510, second laser device 521, quadrant detector 512, quadrant detector 514, mirror 516, mirror 518, beam combiner 520, and optical assembly 526.

Projection head 502 is configured to direct laser beam 428 and detection laser beam 430 into bay 320. Receiver head 506 is configured to receive laser beam 428, detection laser beam 430, and first alignment laser beam 511 at robotic crawler 425. Depending on the implementation, projection head 502 and receiver head 506 may be implemented in a number of different ways. For example, each of projection head 502 and receiver head 506 may be implemented using any number of mirrors, steering mirrors, galvanometer mirrors, gimbaled mirrors, and/or other types of optical elements or devices. Further, each of projection head 502 and receiver head 506 may have an aperture through which laser beams are allowed to pass.

Prior to beginning inspection within bay 320, robotic crawler 425 may need to be aligned with projection head 502. In one illustrative example, robotic crawler 425 may be positioned in front of projection head 502 at some selected location within bay 320. Alignment system 422 is used to search for and locate robotic crawler 425.

In particular, first laser device 510 generates first alignment laser beam 511. First alignment laser beam 511 may be directed towards and injected into articulated beam transfer assembly 426 using mirror 516, mirror 518, and beam combiner 520. Beam combiner 520 directs first alignment laser beam 511 into articulated beam transfer assembly 426 such that first alignment laser beam 511 is substantially collinear with laser beam 428 and detection laser beam 430.

First alignment laser beam 511 is directed towards corner cube 508. Corner cube 508 may be located near the aperture of receiver head 506. In particular, corner cube 508 may be positioned at a known location relative to the aperture of receiver head 506. For example, corner cube 508 may be positioned at some horizontal offset and/or vertical offset relative to the aperture of receiver head 506.

Projection head 502 may be moved such that projection head 502 can direct first alignment laser beam 511 towards corner cube 508. Corner cube 508 may reflect first alignment laser beam 511 back towards projection head 502 in the form of a return signal. Quadrant detector 512 is used to detect this return signal. Projection head 502 may be moved until the return signal detected by quadrant detector 512 is maximized. When the return signal detected by quadrant detector 512 is maximized, robotic crawler 425 is considered as being located by projection head 502.

Similarly, second laser device 521 generates second alignment laser beam 522. Second alignment laser beam 522 is directed by optical assembly 526 towards receiver head 506 and is emitted by receiver head 506 into bay 320. Receiver head 506 may be moved and oriented such that second alignment laser beam 522 is directed towards corner cube 504. Corner cube 504 may be located near the aperture of projection head 502. In particular, corner cube 504 may be positioned at a known location relative to the aperture of projection head 502. For example, corner cube 504 may be positioned at some horizontal offset and/or vertical offset relative to the aperture of projection head 502.

Corner cube 504 reflects second alignment laser beam 522 back towards receiver head 506 in the form of a return signal. This return signal may be directed towards quadrant detector 514 through optical assembly 526. Receiver head 506 may be moved until the return signal detected by quadrant detector 514 is maximized. When the return signal detected by quadrant detector 514 is maximized, projection head 502 is considered as being located by robotic crawler 425.

Additionally, alignment system 422 may also include detector 523 and detector 524. Once projection head 502 has located robotic crawler 425 and once robotic crawler 425 has located projection head 502, further alignment may be achieved using detector 523 and detector 524. For example, the orientation of projection head 502 may be adjusted based on the known offset between corner cube 508 and the aperture of receiver head 506. In this manner, first alignment laser beam 511 may be directed towards the aperture of receiver head 506. Detector 524 may be used to detect first alignment laser beam 511 received through the aperture of receiver head 506. Similarly, the orientation of receiver head 506 may be adjusted based on the known offset between corner cube 504 and the aperture of projection head 502. In this manner, second alignment laser beam 522 may be directed towards the aperture of projection head 502. Detector 523 may be used to detect second alignment laser beam 522 received through the aperture of projection head 502. Proper alignment between projection head 502 and receiver head 506 is achieved when the signals detected at detector 523 and detector 524 are maximized.

In this illustrative example, optical assembly 526 may be implemented using any number of optical elements or devices. For example, optical assembly 526 may be implemented using a plurality of mirrors. Optical assembly 526 is also used to ensure that both laser beam 428 and detection laser beam 430, received at receiver head 506, are directed towards projection system 424.

The orientations of projection head 502 and receiver head 506 may be continuously or periodically changed before and during inspection of bay 320 to ensure that alignment between projection head 502 and receiver head 506 is maintained. In this manner, proper alignment may be achieved throughout the inspection process.

In other illustrative examples, alignment between projection head 502 and robotic crawler 425 may be achieved using a machine vision system or some other type of image-based locating system. This other system may be used in addition to alignment system 422, as part of alignment system 422, or in the place of alignment system 422, depending on the implementation.

In response to receiving laser beam 428 and detection laser beam 430, projection system 424 may project these laser beams onto a location on second surface 410 selected for inspection or onto some other location within bay 320. In this illustrative example, projection system 424 may be implemented using projection head 528. Projection head 528 may be implemented using any number of mirrors, steering mirrors, galvanometer mirrors, gimbaled mirrors, and/or other types of optical elements or devices.

Figure 6:
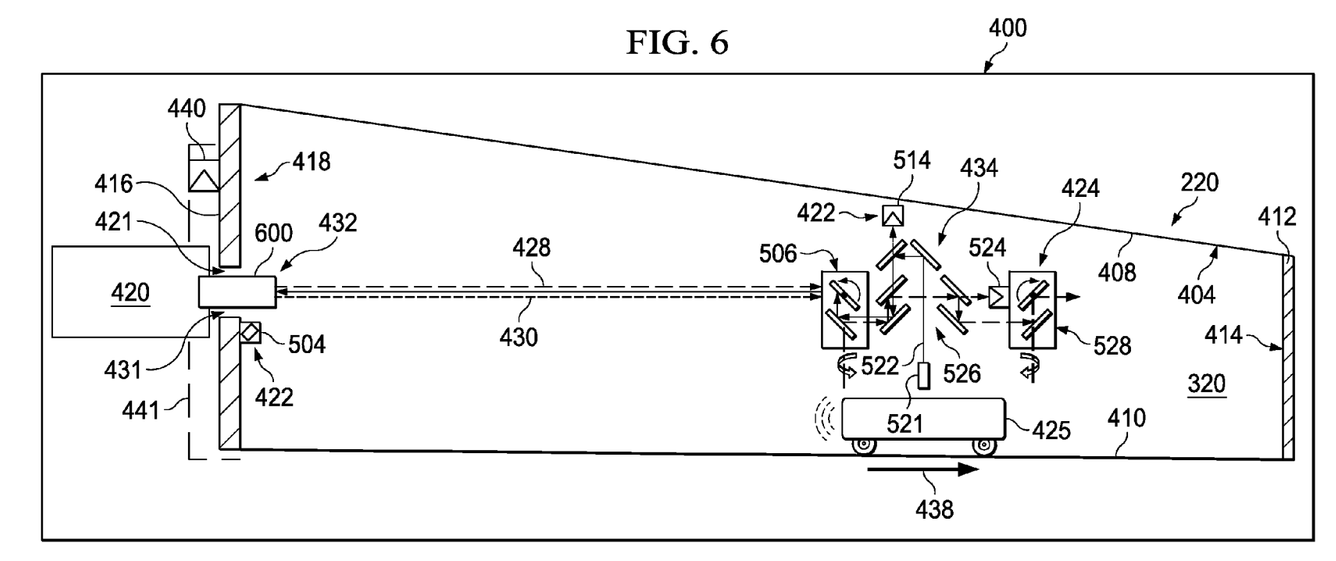
FIG. 6 is an illustration of another configuration for a laser ultrasound testing system in accordance with an illustrative embodiment.

With reference now to FIG. 6, an illustration of another configuration for laser ultrasound testing system 402 from FIG. 5 is depicted in accordance with an illustrative embodiment. In this illustrative example, laser beam 428 and detection laser beam 430 are not transmitted from laser system 420 to projection system 424 using an articulated beam transfer assembly, such as articulated beam transfer assembly 426 in FIGS. 4-5. Rather, laser system 420 emits laser beam 428 and detection laser beam 430 directly into bay 320 through opening 421.

As depicted, in FIG. 6, first setup 432 has a different configuration than first setup 432 in FIG. 5. In FIG. 6, first setup 432 includes scan head 600. In this illustrative example, scan head 600 may be part of laser system 420. However, in other illustrative examples, scan head 600 may be associated with laser system 420 in some other manner. Scan head 600 may be configured to rotate in one or more directions such that the one or more laser beams emitted into bay 320 through scan head 600 may be steered.

In this illustrative example, corner cube 508 from FIG. 5 is not used. Alignment between robotic crawler 425 and scan head 600 is achieved by robotic crawler 425 locating scan head 600 and scan head 600 locating robotic crawler 425. Scan head 600 may be configured to locate robotic crawler 425 using a machine vision system or some other type of image-based locating system. Further, laser system 420 may include a low power laser device (not shown) that may emit an alignment laser beam that may be detected by a detector (not shown) on robotic crawler 425. Scan head 600 may be positioned and oriented such that the signal detected at this detector is maximized. Proper alignment is achieved when the signal is maximized at the detector.

Figure 7:
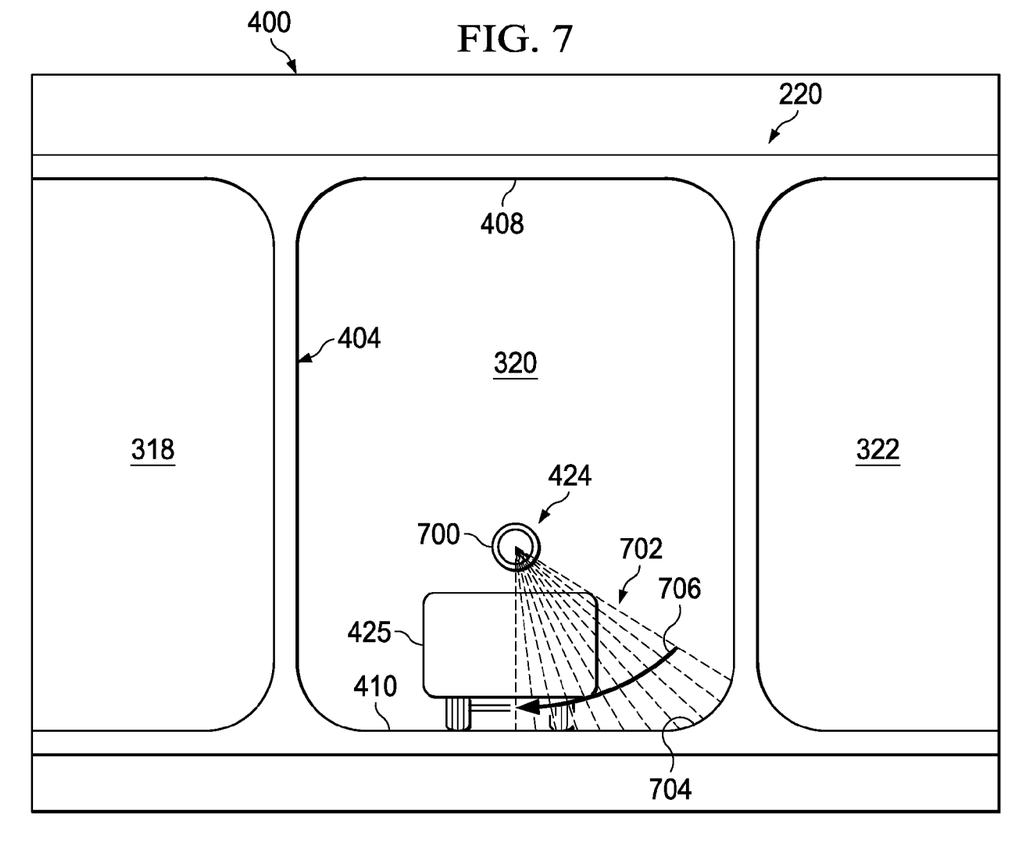
FIG. 7 is an illustration of an end view of a bay in a composite frame in accordance with an illustrative embodiment.

With reference now to FIG. 7, an illustration of an end view of bay 320 from FIG. 6 in a composite frame is depicted in accordance with an illustrative embodiment. In this illustrative example, projection system 424 takes the form of galvanometer scanner 700. Galvanometer scanner 700 may be, for example, a two-axis galvanometer scanner.

Galvanometer scanner 700 is configured to project laser beam 702 onto curved portion 704 of interior surface 404 of bay 320 and scan curved portion 704 using laser beam 702. In particular, galvanometer scanner 700 may move laser beam 702 in the direction of arrow 706 to scan curved portion 704 of interior surface 404.

The illustrations of aircraft 200 in FIG. 2, composite frame 220 in FIG. 3, and testing environment 400 and laser ultrasound testing system 402 in FIGS. 4-7 are not meant to imply physical or architectural limitations to the manner in which an illustrative embodiment may be implemented. Other components in addition to or in place of the ones illustrated may be used. Some components may be optional.

The different components shown in FIGS. 2-7 may be illustrative examples of how components shown in block form in FIG. 1 may be implemented as physical structures. Additionally, some of the components in FIGS. 2-7 may be combined with components in FIG. 1, used with components in FIG. 1, or a combination of the two.

Further, the configurations for alignment system 422 depicted in FIGS. 5-6 are not meant to imply physical or architectural limitations to the manner in which alignment system 422 may be implemented. Any number of other components may be used in addition to the components depicted in FIGS. 5-6.

Figure 8:
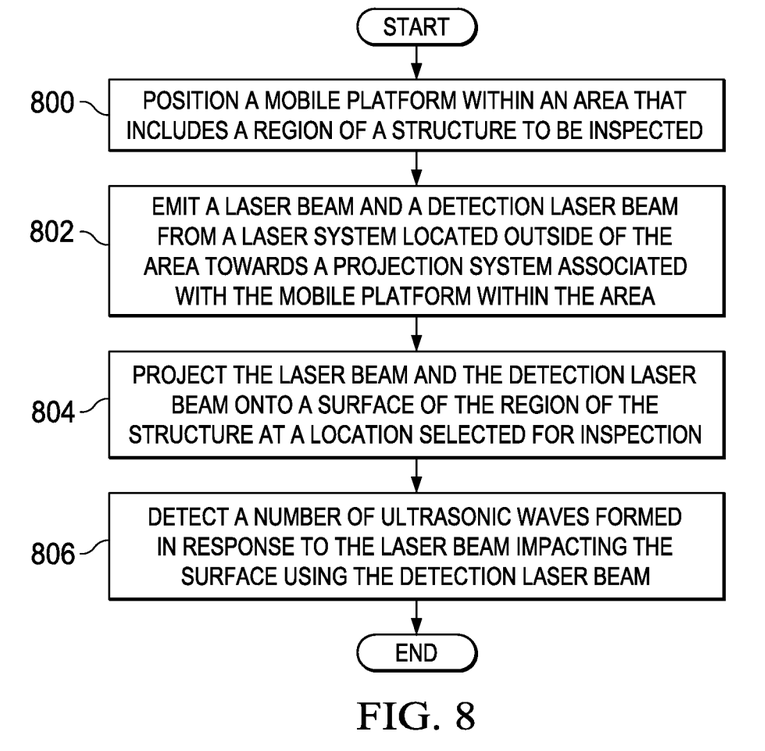
FIG. 8 is an illustration of a process for inspecting a structure in the form of a flowchart in accordance with an illustrative embodiment.

With reference now to FIG. 8, an illustration of a process for inspecting a structure is depicted in the form of a flowchart in accordance with an illustrative embodiment. The process illustrated in FIG. 8 may be implemented using laser ultrasound testing system 102 in FIG. 1.

The process begins by positioning a mobile platform within an area that includes a region of a structure to be inspected (operation 800). The area may be, for example, without limitation, an area to which access is limited. Next, a laser beam and a detection laser beam are emitted from a laser system located outside of the area towards a projection system associated with the mobile platform within the area (operation 802).

In response to receiving the laser beam and the detection laser beam, the projection system projects the laser beam and the detection laser beam onto a surface of the region of the structure at a location selected for inspection (operation 804). A number of ultrasonic waves formed in response to the laser beam impacting the surface are detected using the detection laser beam (operation 806), with the process terminating thereafter. Data generated based on the detection of the ultrasonic waves may be used to identify information about the area.

Figure 9:
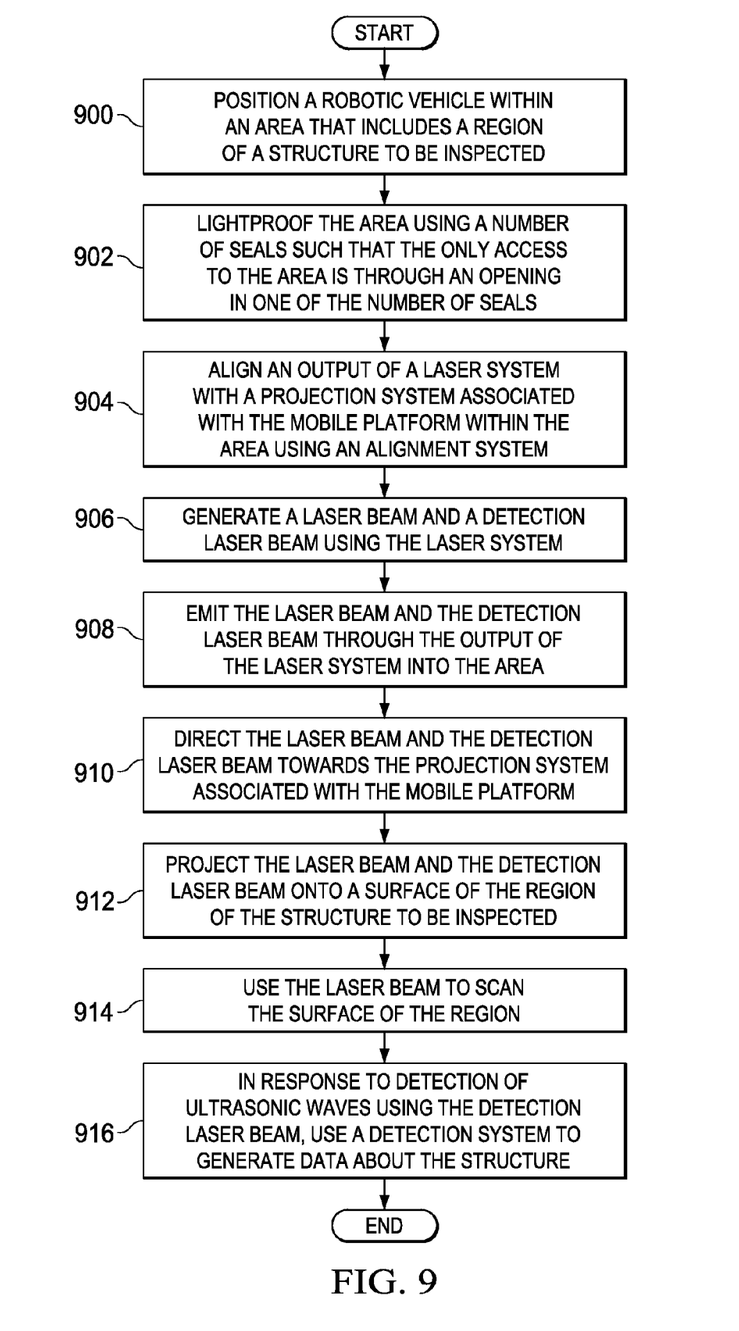
FIG. 9 is an illustration of a process for inspecting a region of a structure within an area in the form of a flowchart in accordance with an illustrative embodiment.

With reference now to FIG. 9, an illustration of a process for inspecting a region of a structure within an area is depicted in the form of a flowchart in accordance with an illustrative embodiment. The process illustrated in FIG. 9 may be implemented using laser ultrasound testing system 102 in FIG. 1.

The process begins by positioning a robotic vehicle within an area that includes a region of a structure to be inspected (operation 900). The structure may be a composite structure. Next, the area is lightproofed using a number of seals such that the only access to the area is through an opening in one of the number of seals (operation 902).

Thereafter, an output of a laser system is aligned with a projection system associated with the mobile platform within the area using an alignment system (operation 904). A laser beam and a detection laser beam are then generated using the laser system (operation 906). The laser beam and the detection laser beam are emitted through the output of the laser system into the area (operation 908). The laser beam and the detection laser beam are directed towards the projection system associated with the mobile platform (operation 910).

The projection system projects the laser beam and the detection laser beam onto a surface of the region of the structure to be inspected (operation 912). The projection system uses the laser beam to scan the surface of the region (operation 914). During operation 912 and operation 914, a number of ultrasonic waves may be formed in the structure.

A detection system is used to generate data about the structure in response to detection of ultrasonic waves using the detection laser beam (operation 916), with the process terminating thereafter. The data generated in operation 916 may be used to generate information about the structure, such as whether any undesired inconsistencies are present in the structure.

Figure 10:
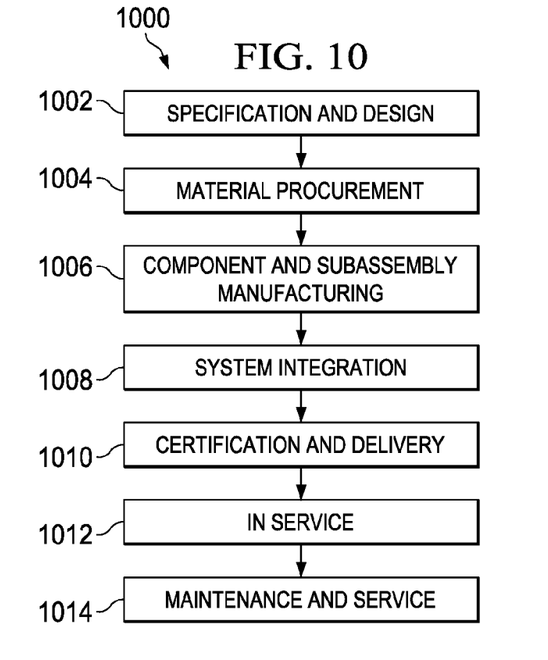
FIG. 10 is an illustration of an aircraft manufacturing and service method in the form of a block diagram in accordance with an illustrative embodiment.
Figure 11:
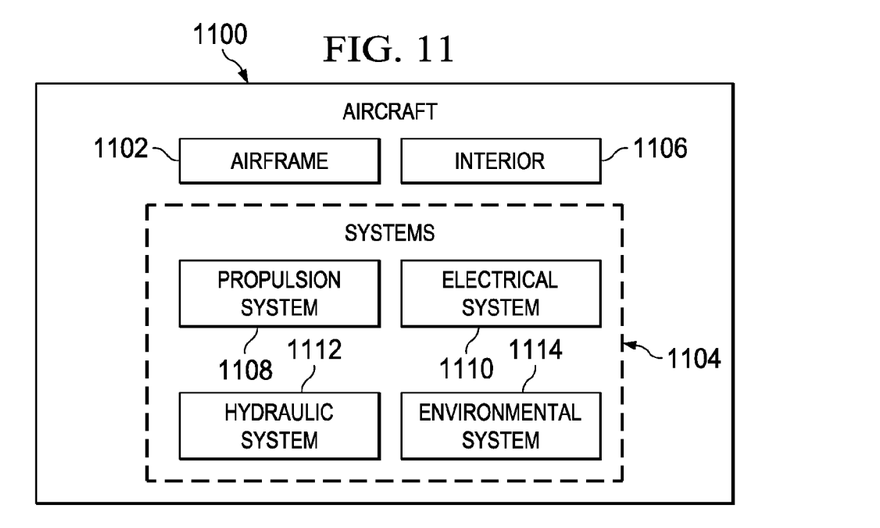
FIG. 11 is an illustration of an aircraft in the form of a block diagram in accordance with an illustrative embodiment.

Illustrative embodiments of the disclosure may be described in the context of aircraft manufacturing and service method 1000 as shown in FIG. 10 and aircraft 1100 as shown in FIG. 11. Turning first to FIG. 10, an illustration of an aircraft manufacturing and service method is depicted in the form of a block diagram in accordance with an illustrative embodiment. During pre-production, aircraft manufacturing and service method 1000 may include specification and design 1002 of aircraft 1100 in FIG. 11 and material procurement 1004.

During production, component and subassembly manufacturing 1006 and system integration 1008 of aircraft 1100 in FIG. 11 takes place. Thereafter, aircraft 1100 in FIG. 11 may go through certification and delivery 1010 in order to be placed in service 1012. While in service 1012 by a customer, aircraft 1100 in FIG. 11 is scheduled for routine maintenance and service 1014, which may include modification, reconfiguration, refurbishment, and other maintenance or service.

Each of the processes of aircraft manufacturing and service method 1000 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of an aircraft is depicted in the form of a block diagram in which an illustrative embodiment may be implemented. In this example, aircraft 1100 is produced by aircraft manufacturing and service method 1000 in FIG. 10 and may include airframe 1102 with systems 1104 and interior 1106. Examples of systems 1104 include one or more of propulsion system 1108, electrical system 1110, hydraulic system 1112, and environmental system 1114. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1000 in FIG. 10. For example, a laser ultrasound testing system, such as laser ultrasound testing system 102 from FIG. 1, may be used to inspect various components of aircraft 1100 during one or more of the stages of aircraft manufacturing and service method 1000 in FIG. 10. In particular, the laser ultrasound testing system may be used to inspect components of aircraft 1100 during component and subassembly manufacturing 1006, system integration 1008, certification and delivery 1010, in service 1012, routine maintenance and service 1014, and/or some other stage of aircraft manufacturing and service method 1000.

In one illustrative example, components or subassemblies produced in component and subassembly manufacturing 1006 in FIG. 10 may be fabricated or manufactured in a manner similar to components or subassemblies produced while aircraft 1100 is in service 1012 in FIG. 10. As yet another example, one or more apparatus embodiments, method embodiments, or a combination thereof may be utilized during production stages, such as component and subassembly manufacturing 1006 and system integration 1008 in FIG. 10. One or more apparatus embodiments, method embodiments, or a combination thereof may be utilized while aircraft 1100 is in service 1012 and/or during maintenance and service 1014 in FIG. 10. The use of a number of the different illustrative embodiments may substantially expedite the assembly of and/or reduce the cost of aircraft 1100.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step. For example, one or more of the blocks may be implemented as program code, in hardware, or a combination of the program code and hardware.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
a laser system located outside of an area that includes a region of a structure to be inspected, wherein the laser system generates a laser beam;
a mobile platform located within the area, wherein the mobile platform is a robotic vehicle configured to move on a surface of the structure;
an alignment system configured to direct the laser beam towards the mobile platform as the mobile platform moves on the surface of the structure, the alignment system comprising a fixed portion and a mobile portion, wherein the fixed portion has a fixed position relative to an output of the laser system, and the mobile portion is positioned on the mobile platform; and wherein the fixed portion steers the laser beam towards the mobile portion on the mobile platform such that the mobile portion receives the laser beam from the fixed portion; and a projection system on the mobile platform, wherein the projection system receives the laser beam from the mobile portion and projects the laser beam onto the surface of the region of the structure and wherein the laser beam causes a number of ultrasonic waves to form within the structure.

2. The apparatus of claim 1 further comprising:
a transmission system configured to guide the laser beam from the laser system to the output of the laser system.

3. The apparatus of claim 1 further comprising:
a number of seals configured to lightproof the area such that light is allowed into the area through an opening in one of the number of seals, wherein the laser beam is emitted through the opening into the area.

4. The apparatus of claim 1, wherein the alignment system comprises at least one of a mirror, a prism, a lens, a rotating diffraction grating, a mirror-based gimbal system, a beam-director unit, a galvanometer, a mirror galvanometer, a galvanometer scanner, a detector, or a quadrant cell detector.

5. The apparatus of claim 1, wherein the projection system comprises at least one of a mirror, a prism, a lens, a rotating diffraction grating, a mirror-based gimbal system, a beam-director unit, a galvanometer, a mirror galvanometer, or a galvanometer scanner.

6. The apparatus of claim 1, wherein the laser system is further configured to generate a detection laser beam and wherein the projection system is configured to receive the detection laser beam and project the laser beam onto the surface of the region of the structure.

7. The apparatus of claim 6 further comprising:
a detection system configured to measure an alteration in the detection laser beam caused by the number of ultrasonic waves.

8. The apparatus of claim 1, wherein the mobile platform is a robotic crawler.

9. The apparatus of claim 1 further comprising:
a control unit configured to control movement of the mobile platform within the area and a location at which the laser beam is projected onto the surface of the area.

10. The apparatus of claim 1, wherein the projection system comprises a galvanometer scanner.

11. The apparatus of claim 1 further comprising:
a positioning system configured for use in positioning the mobile platform within the area.

12. A laser ultrasound testing system comprising:
a laser system located outside of an area that includes a region of a structure to be inspected, wherein the laser system is configured to emit a laser beam and a detection laser beam through an output of the laser system;
a mobile platform located within the area, wherein the mobile platform is a robotic vehicle configured to move on a surface of the structure;
an alignment system configured to direct the laser beam towards the mobile platform as the mobile platform moves on the surface of the structure, the alignment system comprising a fixed portion and a mobile portion, wherein the fixed portion has a fixed position relative to the output of the laser system, and the mobile portion is positioned on the mobile platform; and wherein the fixed portion steers the laser beam towards the mobile portion on the mobile platform such that the mobile portion receives the laser beam from the fixed portion; and
a projection system on the mobile platform, wherein the projection system receives the laser beam and the detection laser beam from the mobile portion, and projects the laser beam and the detection laser beam onto the surface of the region of the structure and wherein the laser beam causes a number of ultrasonic waves to form within the structure.

13. The laser ultrasound testing system of claim 12 further comprising:
a detection system configured to measure an alteration in the detection laser beam caused by the number of ultrasonic waves.

14. A method for inspecting a structure, the method comprising:
positioning a mobile platform within an area that includes a region of the structure to be inspected, wherein the mobile platform is a robotic vehicle configured to move on a surface of the structure;
emitting a laser beam from a laser system located outside of the area steering the laser beam from an output of the laser system to direct the laser beam from the laser system towards the mobile platform such that the mobile platform receives the laser beam from the laser system as the mobile platform moves on the surface of the structure; and
projecting the laser beam received by the mobile platform onto the surface of the region of the structure at a location selected for inspection by a projection system on the mobile platform, wherein a number of ultrasonic waves are formed in the structure in response to the laser beam impacting the surface.

15. The method of claim 14 further comprising:
emitting a detection laser beam from the laser system;
projecting the detection laser beam onto the surface of the region of the structure at the location using the projection system; and
detecting the number of ultrasonic waves formed in the structure using the detection laser beam.

16. The method of claim 14 further comprising:
scanning the surface of the region of the structure using the projection system.

17. The method of claim 14, wherein steering the laser beam from the output of the laser system towards the mobile platform is performed using a fixed portion of an alignment system, wherein the fixed portion has a fixed position relative to the output of the laser system; and
the mobile platform receives the laser beam by a mobile portion of the alignment system on the mobile platform.

18. The method of claim 14, further comprising:
lightproofing the area prior to emitting the laser beam into the area.

19. The apparatus of claim 3, further comprising:
a detector system comprising one or more detectors positioned around the number of seals, wherein the detector system is configured detect light from the laser beam that escapes from the area.

* * * * *